Jan. 20, 1948. M. J. JOHNSON Plant Pat. 780
STRAWBERRY PLANT
Filed Oct. 21, 1946
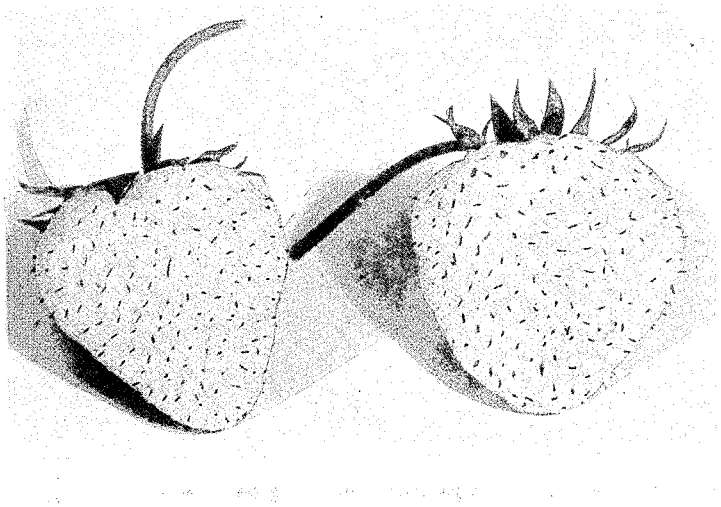
Inventor:
M. J. Johnson
By Robert Robb
Attorneys Patented Jan. 20, 1948

Plant Pat. 780

UNITED STATES PATENT OFFICE

780

STRAWBERRY PLANT

Matthew James Johnson, Thornhill, Ontario, Canada, assignor to the R. M. Kellogg Company, Three Rivers, Mich.

Application October 21, 1946, Serial No. 704,573

1 Claim. (Cl. 47—62)

My invention relates to a new and distinct variety of strawberry plant, the result of a cross between "Premier" and "Bedarena."

The object of this cross was to produce a new strawberry plant having certain of the desirable characteristics of its parents.

It is well known that Premier is considered to be one of the best varieties marked by its very early and extra long fruiting season, its high frost resistance, and its resistance to disease and drought, as well as its moderately sweet flavor. On the other hand the variety Bedarena has little to recommend it except its sweet and aromatic flavor of the berry.

The crossing of the two parents of the present variety was therefore the result of a definite effort to produce a new variety of plant having the general characteristics of Premier but with the better and sweeter flavor of Bedarena. The result of this hybridization is the production of the present new and distinct variety having substantially all of the good characteristics of Premier with improvement in some of those characteristics and with the sweeter and better flavor of Bedarena.

My new variety has approximately the same very early and extra long fruiting season as Premier except that my new variety ripens a few days later, usually about three or four days after Premier. The fruiting season of my new variety is about three to four weeks, the first commercial picking being about June 15th and the last commercial picking being about July 6th, the region of Thornhill, Ontario. My new variety has about the same large size of berries as Premier but differs somewhat in shape from Premier. Like Premier the shape of the berries of my new variety is conical but they are not so long and are more blunt; and whereas Premier has a large percentage of double berries, my new variety has only a relatively few doubles. The color of the berries of my new variety is slightly darker red than Premier and like the latter the color goes clear to the center.

My new variety has similar characteristics to those of Premier in reference to frost resistance and disease resistance, being seldom touched by leaf spot or other fungus diseases and it stands excessive moisture or excessive drought exceedingly well. My new variety is a much stronger plant than Premier and much better than Premier for heavier soil.

Probably the most striking characteristic of my new variety is in the flavor. While the flavor of Premier is moderately sweet, it is usually better when eaten with sugar. My new variety has a distinctively different flavor similar to that of Bedarena. It is palatably sweet and needs no sugar though the sweetness is not at all cloying and is combined with a mild and palatable aromatic character.

Typical berries of my new variety of strawberry plant are shown in the accompanying drawing forming a part thereof.

Following is a detailed description of my new variety, observations being made from plants growing in Thornhill, Ontario, Canada:

Plant: Growth — medium. Root — vigorous. Crown—large.

*Leaves.*—Many; medium. Petiole length—medium. Color — medium green. Pubescence—medium; spreading. Groove—shallow. Petiole of central leaflet is one-third longer than that of the lateral blade; central leaflet equals lateral. Serrations—regular, the teeth broadly ovate-ciliate; apex tinged red; those of central leaflet extend over upper two-thirds of margin. Leaflet surface—Upper: glossy, smooth, curled. Color—medium green; color lower surface—light green. Pubescence — medium.

*Runners.*—Appear after fruiting; numerous; medium.

*Flower stems.*—Medium; inflorescence exposed.

*Bloom.*—Early. Date first bloom—varies according to season. Flowers — many. Breadth—primary, 1 inch; secondary, ¾ inch; perfect.

*Fruiting stems.*—Medium; stout; upright. Radical—shorter than main truss. Branches of truss—many.

*Sex.*—Bi-sexual.

*Soil where grown.*—Loamy; well drained.

*Culture.*—Frequent.

*Disease resistance.*—Plant seldom touched by leaf spot or other fungus diseases. Extra healthy.

*Insect resistance.*—Medium.

*Frost resistance.*—Extra resistant.

*Rain and drought resistance.*—Stands excessive moisture or excessive drought exceedingly well.

Fruit: Condition when described—prime; date described—June 25.

*Size.*—Uniform; large; decreases late in season.

*Form.*—Uniform; regular; conical. Apex—truncate.

*Stems.* — Radical — medium - short. Main truss — medium - short. Pubescence — scant.

*Calyx.*—Green after picking; raised; free; medium. Upper surface color—light; pubescence — scant. Lower surface — light green; pubescence—scant.

*Surface.*—Green tips—few; seeds—inconspicuous; depressed below surface.

*Core.*—Solid.

*Flesh.*—Juicy. Color—slightly darker than "Premier." Texture—firm; fine; melting.

*Flavor.*—Palatably sweet and mildly aromatic.

*Quality.*—Best; shipping quality—good.

*Use.*—Market—dessert.

The primary characteristics referred to have been found to be fixed in the asexual reproduction of the plant.

I claim:

A new and distinct variety of strawberry plant substantially as hereindisclosed, characterized as to novelty by its vigorous growth, stronger plant, the large size and blunt conical shape of its berries, the darker red color and palatably sweet and mildly aromatic flavor of the berries.

MATTHEW JAMES JOHNSON.